United States Patent
Franco-Tabares

(10) Patent No.: US 12,145,845 B2
(45) Date of Patent: Nov. 19, 2024

(54) METHOD FOR PRODUCING FLUORAPATITE CRYSTALS

(71) Applicant: NANO DENTICA AB, Gothenburg (SE)

(72) Inventor: Sebastian Franco-Tabares, Gothenburg (SE)

(73) Assignee: NANO DENTICA AB, Gothenburg (SE)

( * ) Notice: Subject to any disclaimer, the term of this patent is extended or adjusted under 35 U.S.C. 154(b) by 0 days.

(21) Appl. No.: 18/262,580

(22) PCT Filed: Jan. 27, 2022

(86) PCT No.: PCT/EP2022/051948
§ 371 (c)(1),
(2) Date: Jul. 24, 2023

(87) PCT Pub. No.: WO2022/162091
PCT Pub. Date: Aug. 4, 2022

(65) Prior Publication Data
US 2024/0043275 A1     Feb. 8, 2024

(30) Foreign Application Priority Data

Jan. 28, 2021   (SE) .................................. 2130026-4

(51) Int. Cl.
| | |
|---|---|
| *C01B 25/455* | (2006.01) |
| *A61K 6/20* | (2020.01) |
| *A61K 6/75* | (2020.01) |

(52) U.S. Cl.
CPC .............. *C01B 25/455* (2013.01); *A61K 6/20* (2020.01); *A61K 6/75* (2020.01); *C01P 2002/72* (2013.01); *C01P 2002/82* (2013.01); *C01P 2002/85* (2013.01); *C01P 2004/03* (2013.01); *C01P 2004/04* (2013.01)

(58) Field of Classification Search
None
See application file for complete search history.

(56) References Cited

U.S. PATENT DOCUMENTS

| | | | |
|---|---|---|---|
| 4,157,378 | A | 6/1979 | Duff et al. |
| 7,879,388 | B2 | 2/2011 | Clarkson et al. |
| 2009/0060814 | A1 | 3/2009 | Ishikawa et al. |
| 2010/0255306 | A1 | 10/2010 | Ishikawa et al. |
| 2012/0128566 | A1 | 5/2012 | Wei et al. |

FOREIGN PATENT DOCUMENTS

| | | |
|---|---|---|
| JP | 01264915 A | 10/1989 |
| JP | 2013/203563 A | 10/2013 |
| JP | 2014181160 | 9/2014 |

OTHER PUBLICATIONS

International Search Report and Written Opinion were mailed on Apr. 20, 2022 by the International Searching Authority for International Application No. PCT/EP2022/051948 filed on Jan. 27, 2022 and published as WO2022162091 (Applicant- Nano Dentica AB) (10 pages).
International Preliminary Report on Patentability issued on Feb. 13, 2023 by the International Searching Authority for International Application No. PCT/EP2022/051948 filed on Jan. 27, 2022 and published as WO 2022162091 (Applicant- Nano Dentica AB) (14 pages).
Hongyou et al., "Size-controlled synthesis and characterization of fluorapatite nanocrystals in the presence of gelatin", Powder Technology, vol. 209, No. 1 2011, pp. 9-14.
Apatite R050192—RRUFF Database: Raman, X-ray, Infrared, and Chemistry [Internet]. [cited 25 021 Jan. 22]. Available from: https://rruff.info/Apatite/R050192.
Chen H, et al. Acellular Synthesis of a Human Enamel-like Microstructure. Adv Mater. Jul. 18, 2006;18(14):1846-51.
Chen M, et al. Controllable synthesis of fluorapatite nanocrystals with various morphologies: Effects of pH value and chelating reagent. Journal of Alloys and Compounds. Oct. 19, 2009;485(1-2):396-401.
Enax J, et al. Ultrastructural organization and micromechanical properties of shark tooth enameloid. Acta Biomaterilia. 2014;10(9):3959-68.
Farr T D, et al. System CaO—P2O5—HF—H2O: Equilibrium at 25 and 50°. J. Phys. Chem. 1962;66(2):318-21.
Fluorapatite R060421—RRUFF Database: Raman, X-ray, Infrared, and Chemistry [Internet]. [cited Jan. 22, 2021]. Available from: https://rruff.info/fluorapatite/R060421.

(Continued)

*Primary Examiner* — Tanisha Diggs
(74) *Attorney, Agent, or Firm* — Ballard Spahr LLP

(57) ABSTRACT

Described is a method for producing fluorapatite crystals, the method having the steps of:

a) providing a first aqueous solution comprising a phosphate source and a fluoride source, said first aqueous solution being supersaturated with respect to the phosphate source and the fluoride source, b) providing a second aqueous solution comprising a calcium source, said second aqueous solution being unsaturated with respect to the calcium source, c) mixing the first aqueous solution and the second aqueous solution thereby providing a mixture containing fluorapatite crystals and a further aqueous solution, d) optionally stirring the mixture of step c), e) optionally heating the mixture of step c) and/or step d), f) separating the fluorapatite crystals from the further aqueous solution, g) optionally drying the fluoroapatite crystals of step f), and h) optionally milling the fluorapatite crystals obtained in step f) or step g).

20 Claims, 11 Drawing Sheets

(56) References Cited

OTHER PUBLICATIONS

Kniep R, et al. Fluorapatite-Gelatine-Nanocomposites: Self-Organized Morphogenesis, Real Structure and Relations to Natural Hard Materials. In: Naka K, editor. Biomineralization I [Internet]. Springer Berlin Heidelberg; 2006 [cited May 17, 2016]. p. 73-125. (Topics in Current Chemistry). Available from: http://link.springer.com/chapter/10.1007/128_053.

Konttinen M-L, et al. Fluoride concentrations of the surface enamel of children living in an optimally fluoridated community. Scand J Dent Res. 1986; 94(5):427-35.

Montel G. Contribution à l'étude des mécanismes de synthèse de la fluorapatite. [Paris]; 1958.

Müller F, et al. Elemental Depth Profiling of Fluoridated Hydroxyapatite: Saving Your Dentition by the Skin of Your Teeth? Langmuir. 2010;26(24):18750-9.

Nedeljkovic I, et al. Secondary caries: prevalence, characteristics, and approach. Clin Oral Investig. 2020;24(2):683-91.

Sousa R A, et al. Coupling of HDPE/hydroxyapatite composites by silane-based methodologies. J Mater Sci Mater Med. Jun. 2003;14(6):475-87.

Wang H, et al. Size-controlled synthesis and characterization of fluorapatite nanocrystals in the presence of gelatin. Powder Technol. 2011;209(1):9-14.

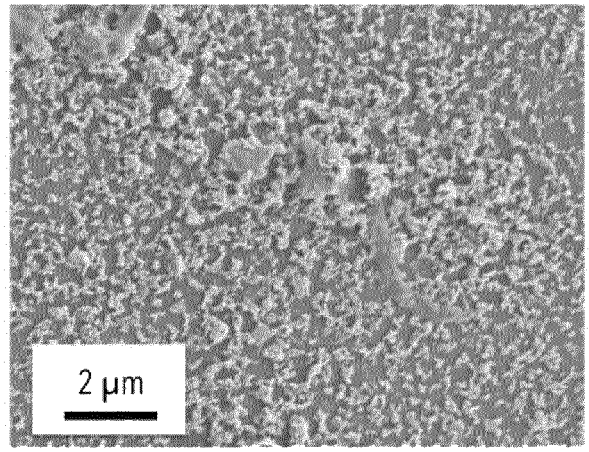
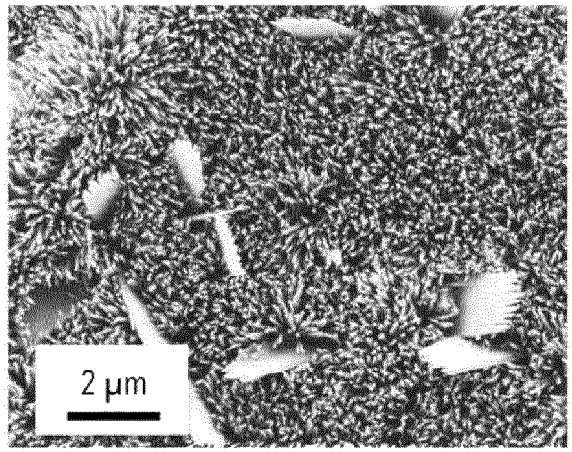
Figure 7A
Figure 7B
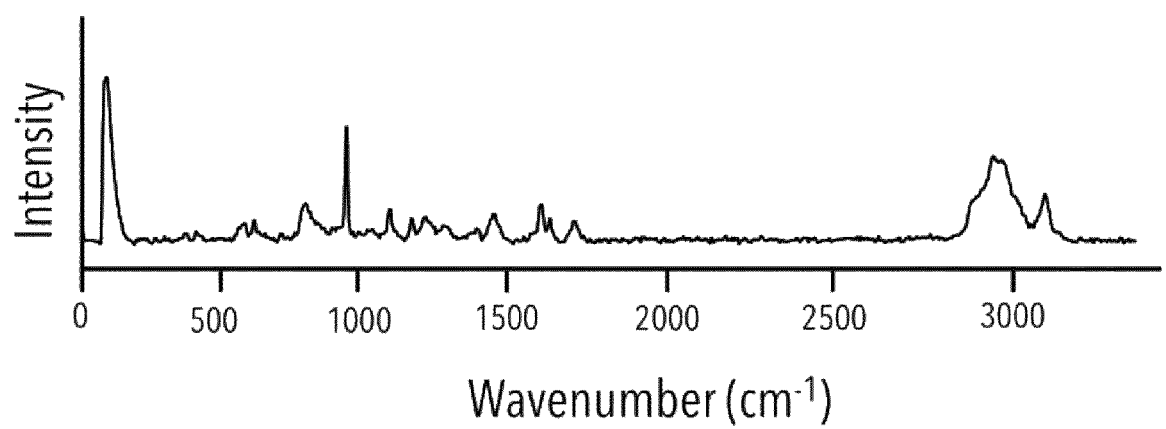
Figure 7C

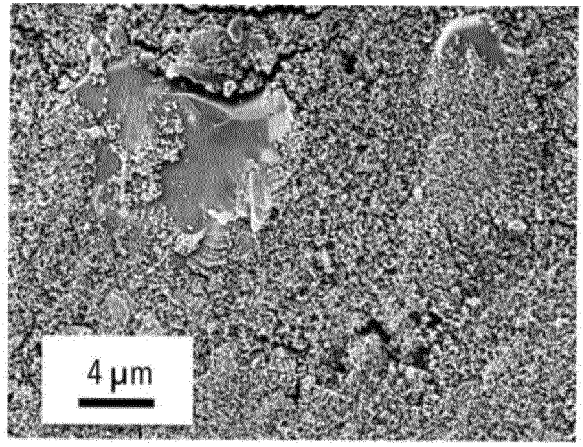
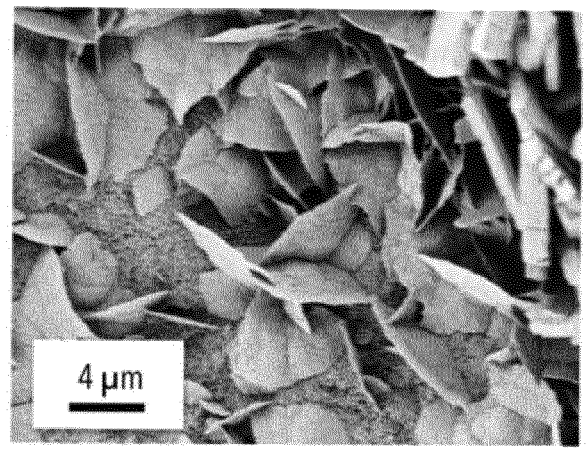
Figure 8A  Figure 8B
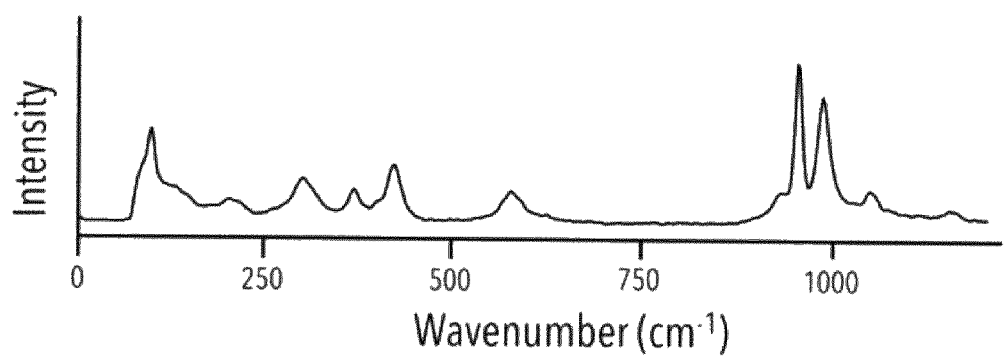
Figure 8C

METHOD FOR PRODUCING FLUORAPATITE CRYSTALS

CROSS REFERENCE TO RELATED APPLICATIONS

This application is a U.S. National Phase Application of International Application No. PCT/EP2022/051948, filed Jan. 27, 2022, which claims priority to Swedish Patent Application No. 2130026-4, filed Jan. 28, 2021, each of which are hereby incorporated by reference in their entirety.

TECHNICAL FIELD

The present disclosure relates to a method for producing fluorapatite crystals. The fluorapatite crystals may be nanofluorapatite crystals or microfluorapatite crystals. The present disclosure also relates to use of the aforementioned fluorapatite crystals for producing a liner, a sealer, a ceramic material, a dental restorative product, a filling material such as a dental cement composition; a coating for teeth, implant or a medical device.

BACKGROUND

Fluorapatite ($Ca_5(PO_4)_3F$) is the most common phosphate mineral widely occurring along the Earth's crust playing a significant role for the soil fertilizer industry. It is also found in the form of complex packed-structures in the superficial layer of sharks' dentition, which is specialized for hunting and biting (Reference 1). Fluorapatite is not naturally present in the human dentition. It is, hydroxyapatite ($Ca_5(PO_4)_3OH$) instead that is present on its superficial layer or enamel (Reference 1).

Within oral sciences, its main application is related to its ability to prevent dental caries by either fluoridation of water or topical application of fluoride-containing products (toothpastes, varnishes, mouthwashes, among others). The World Health Organization states that fluoridation of water can reduce significantly the risk to dental caries among children and has been related to higher concentrations of $F^-$ on the most superficial layers of enamel during tooth formation and subsequently tooth eruption, indicating the presence of fluorapatite (Reference 2). Additionally, it has been showed that the topical application of fluoride is reflected in the transformation of hydroxyapatite to fluorapatite on the most superficial layers of enamel, specifically, few atomic layers (Reference 3). Moreover, fluorapatite could aid in the management and prevention of secondary caries (SC). A recent study presented that SC is correlated with class II composite restorations, in patients with high caries risk who smoke. Additionally, that SC may affect 20% of the patients on private practices, in which the most common treatment is replacement of the restoration (Reference 4). A frustrating and costly process for patients and clinicians.

Different approaches to the synthesis of powdered fluorapatites have been previously described. For instance, Montel G. showed his doctoral thesis in 1958 that fluorapatite can be produced by solid state reactions including mixtures of calcium fluoride ($CaF_2$) and tetracalcium phosphate (TCP) or calcium pyrophosphate ($Ca_2P_2O_7$) heated at 900° C. for two hours. The same author showed that fluorapatite can be produced by hydrothermal reactions. A typical reaction uses disodium phosphate ($Na_2HPO_4$) and calcium chloride ($CaCl_2$) in ammonia to synthetize dicalcium phosphate dihydrate ($CaHPO_4 \cdot 2H_2O$). And calcium chloride ($CaCl_2$) and sodium fluoride ($NaF_2$) to produce calcium fluoride ($CaF_2$). Then, dicalcium phosphate dihydrate ($CaHPO_4 \cdot 2H_2O$) and calcium fluoride ($CaF_2$) are mixed and constantly stirred at room temperature at 50 rpm for 5 days. A faster reaction, reports Montel G., can be obtained by mixing dicalcium phosphate dihydrate ($CaHPO_4 \cdot 2H_2O$) and sodium fluoride ($NaF_2$)(Reference 5).

Later, it was documented by Farr T D. et al in 1962 that fluorapatite can be obtained after the equilibration of phosphoric acid ($H_3PO_4$), alpha-tetracalcium phosphate (α-TCP), monocalcium monophosphate (MCPM) and calcium fluoride at 50° C. for 7 months (Reference 6). By 2006, Kniep R. and Simon P. introduced the use of nucleation agents as key factors for the synthesis. For instance, fluorapatite of 2-20 μm (rod, fan-like and spherical) can be produced using pig skin gelatin as nucleating and growth agent by diffusing two solutions into the central gelatin. The solutions are typically calcium chloride ($CaCl_2$) as a calcium source and disodium phosphate ($Na_2HPO_4$) with potassium fluoride (KF) as the phosphate and fluoride source. Both solutions adjusted to a pH of 7.4. The reaction occurs between 25° C. and 30° C. during 3 weeks (Reference 7).

Chen H. et al reported also in 2006 the use of chelating agent ethylenediaminetetraacetic acid (EDTA). Fluorapatite powders are produced by mixing ethylenediaminetetraacetic acid calcium disodium salt (EDTA-Ca—$Na_2$) and sodium phosphate dihydrate ($Na_2HPO_4 \cdot H_2O$). The pH of the solution is adjusted to 6.0 by sodium hydroxide (NaOH). Then, a sodium fluoride (NaF) solution is added and stirred for several minutes at room temperature. Subsequently, the mixture is then autoclaved at 121° C. at 2.37 atm for 5 minutes to 10 hours (Reference 8).

Chen M. et al introduced in 2009 the use of citric acid to produce fluorapatite. It is mixed with disodium ethylenediaminetetraacetic acid ($Na_2$EDTA) and kept in water bath at 40° C. Then, calcium nitrate ($Ca(NO_3)_2$), diammonium phosphate (($NH_4)_2HPO_4$) and sodium fluoride (NaF) are added under constant stirring. The pH is adjusted to 5.2 using sodium hydroxide (NaOH). Then the mixture is stirred for 20 min and later autoclaved at 150° C. for 8 hours (Reference 9).

Clarkson B H and Chen H patented in 2011 (U.S. Pat. No. 7,879,388B2) a method in which hydroxyapatite itself is used as the starting source of calcium and phosphate to produce fluorapatite powders. Hydroxyapatite is mixed with sodium fluoride and both dissolved with nitric acid. Then, the pH is adjusted to 6-11 using ammonium hydroxide. The solution is then left in water bath at 25-70° C. for 5 days (Reference 10).

Wang H. et al reported in 2011 that fluorapatite crystals can be produced by using acetic acid. A calcium chloride ($CaCl_2$) solution is mixed with a sodium phosphate dodecahydrate ($Na_2HPO_4 \cdot 12H_2O$) and a sodium fluoride (NaF) solution. Acetic acid and sodium hydroxide are used to keep the solutions pH below 6. The two solutions are mixed and kept in a water bath at 37° C. for 1-5 weeks (Reference 11).

More recently, Furukawa A. patented in 2014 (JP2014181160A) a method to produce fluorapatite crystals can be produced by the constant stirring of two solutions that are mixed by a drop-funnel. Typically, the calcium source is calcium chloride dihydrate ($CaCl_2 \cdot 2H_2O$) which is adjusted to pH=5.0 by hydrochloric acid (HCl). The phosphate and fluoride solution is typically a combination of diammonium phosphate (($NH_4)_2HPO_4$) or hydrogen dihydrogen phosphate $H(H_2PO_4)$ with sodium fluoride ($NaF_2$), its pH is also adjusted to 5.0 by hydrochloric acid (HCl). The reaction occurs at 50° by constant sitting for 1 hour, in which the pH of the reaction is adjusted to 5.0 or less. The solution can be added to each other by a drop funnel or to a water solution at the mentioned temperature. The resultant fluorapatite crystals are bundle-like and require an additional step of dispersion using polyphosphoric acid salt using a shake treatment by means of zirconia beads for 6 hours (Reference 12).

The great value that fluorapatite represents for preventive and restorative dentistry is limited by the industrial capability of producing powders by a simple and rapid method. For instance, the method proposed by Montel G. occurs at room temperature but requires constant stirring at 50 rpm and 5 days reaction time. A reaction time that is impractical for industrial applications.

The method reported by Farr T D et al involves a process of 5 months reaction time. A reaction time that is unfeasible for industrial applications.

The method documented by Kniep R. & Simon P. uses gelatin skin, three-week reaction time, requires pH adjustment and can only produce micro crystals. A process that cannot produce nanofluorapatite and with and too long reaction time for industrial purposes.

The method described by Chen H. et al requires an increased atmospheric pressure (2.37 atm) at 121° C. and a reaction time that can last 10 hours. A complicated process with limited industrial scalability.

The method presented by Chen M. et al requires pH adjustment, elevated atmospheric pressures in an autoclave and 150° C. with 8 hours reaction time. Also, a complex process limited by its industrial scalability.

The method reported by Clarkson B H. and Chen H. (U.S. Pat. No. 7,879,388B2) requires pH adjustment and 5 days reaction time. A method rather unfeasible for industrial applicability.

The method documented by Wang H. et al requires pH adjustment and one to five-weeks reaction time. Also, a too long reaction time for industrial purposes.

The method described by Furukawa A (JP2014181160A) requires pH adjustment and constant stirring for one hour, and its unable to produce individual nanofluorapatite crystals. The structures produced are bundle-like and require six hours milling in polyphosphoric acid in order to produce individual crystals. A method that lacks simplicity and requires milling to produce individual nanofluorapatite crystals, that also lacks the capability of producing microfluorapatite crystals.

The majority of the mentioned methods are naturally based on the reactants proposed by Montel G. in 1958. However, they require pH adjusting, constant stirring, extensive milling, reaction temperatures above 100° C. and/or increased atmospheric pressures. Hence, they are still costly procedures on an industrial scale, making those fluorapatite powders still unavailable for professionals and patients.

None of them can produce individual nanofluorapatite crystals immediately after mixing and stirring for 1 minute two solutions as proposed in the present patent and none of them can produce individual microfluorapatite crystals after 10 min at 70° C. Moreover, without the need of pH adjustment, constant stirring and prolonged reaction temperatures and/or elevated pressures. Making the present method more suitable for mass-production and industrial scalability.

Additionally, one of the goals strategized by The United Nations General Assembly in 2015 is the sustainable Development Goal (Goal 9 or SDG 9) which aims to build resilient infrastructure, promote sustainable industrialization and foster innovation. One of the mechanisms to achieve this goal is by upgrading all industries and infrastructures for sustainability; enhance research and upgrade industrial technologies.

The listing or discussion of an apparently prior-published document in this specification should not necessarily be taken as an acknowledgement that the document is part of the state of the art or is common general knowledge.

It is an object of the present disclosure to overcome or at least mitigate one of the problems described above. Further, it is an object of the present disclosure to provide advantages and/or aspects not provided by hitherto known technique.

SUMMARY

The above object may be achieved with the method for producing fluorapatite crystals according to claim 1. There is also provided a method for preparing a dental or non-dental composition according to claim 16. Further, there is provided a use of fluorapatite crystals produced in accordance with the method for producing fluorapatite crystals described herein. Variations of the disclosure are set out in the dependent claims and in the following description.

BRIEF DESCRIPTION OF THE DRAWINGS

FIG. 4, graph 2, shows an XRD of a powder as described in Example 1.

FIG. 4, graph 3, shows an XRD of a powder as described in Example 2.

FIG. 4, graph 4, shows an XRD of a powder as described in Example 2.

FIG. 4, graph 5, shows an XRD of a powder as described in Example 3.

FIG. 4, graph 6, shows an XRD of a powder as described in Example 4.

FIG. 4, graph 7, shows an XRD of mineral fluorapatite as described herein.

FIG. 5, graph 2, an RS spectrum of a powder as described in Example 1.

FIG. 5, graph 3, an RS spectrum of a powder as described in Example 2.

FIG. 5, graph 4, an RS spectrum of a powder as described in Example 2.

FIG. 5, graph 5, an RS spectrum of a powder as described in Example 3.

FIG. 5, graph 6, an RS spectrum of a powder as described in Example 4.

FIG. 5, graph 7, an RS spectrum of mineral fluorapatite as described herein.

FIG. 6, graph 2, shows an EDS image of a powder as described in Example 2.

FIG. 6, graph 3, shows an EDS image of a powder as described in Example 3.

FIG. 6, graph 4, shows an EDS image of a powder as described in Example 4.

FIG. 7A shows a SEM image of a pellet as described in Example 5.

FIG. 7B shows a SEM image of a pellet after immersion in artificial saliva as described in Example 5.

FIG. 7C shows an RS spectrum of a polymer-based cement as described in Example 5.

FIG. 8A shows a SEM image of a dried pellet as described in Example 6.

FIG. 8B shows a SEM image of a pellet subjected to deionized water and artificial saliva as described in Example 6.

FIG. 8C shows an RS spectrum of a water-based cement as described in Example 6.

FIG. 10, graph 2, shows an EDS image of a pellet of a microliner comprising water-based 10-MDP containing primer and an ethanol/water free adhesive as described in Example 7 after immersion in artificial saliva.

FIG. 10, graph 3, shows an EDS image of a pellet of a microliner comprising a total etch ethanol-based adhesive as described in Example 7 after immersion in artificial saliva.

FIG. 10, graph 4, shows an EDS image of a pellet of a microliner comprising a total etch water-based adhesive as described in Example 7 after immersion in artificial saliva.

DESCRIPTION

Figure 1:
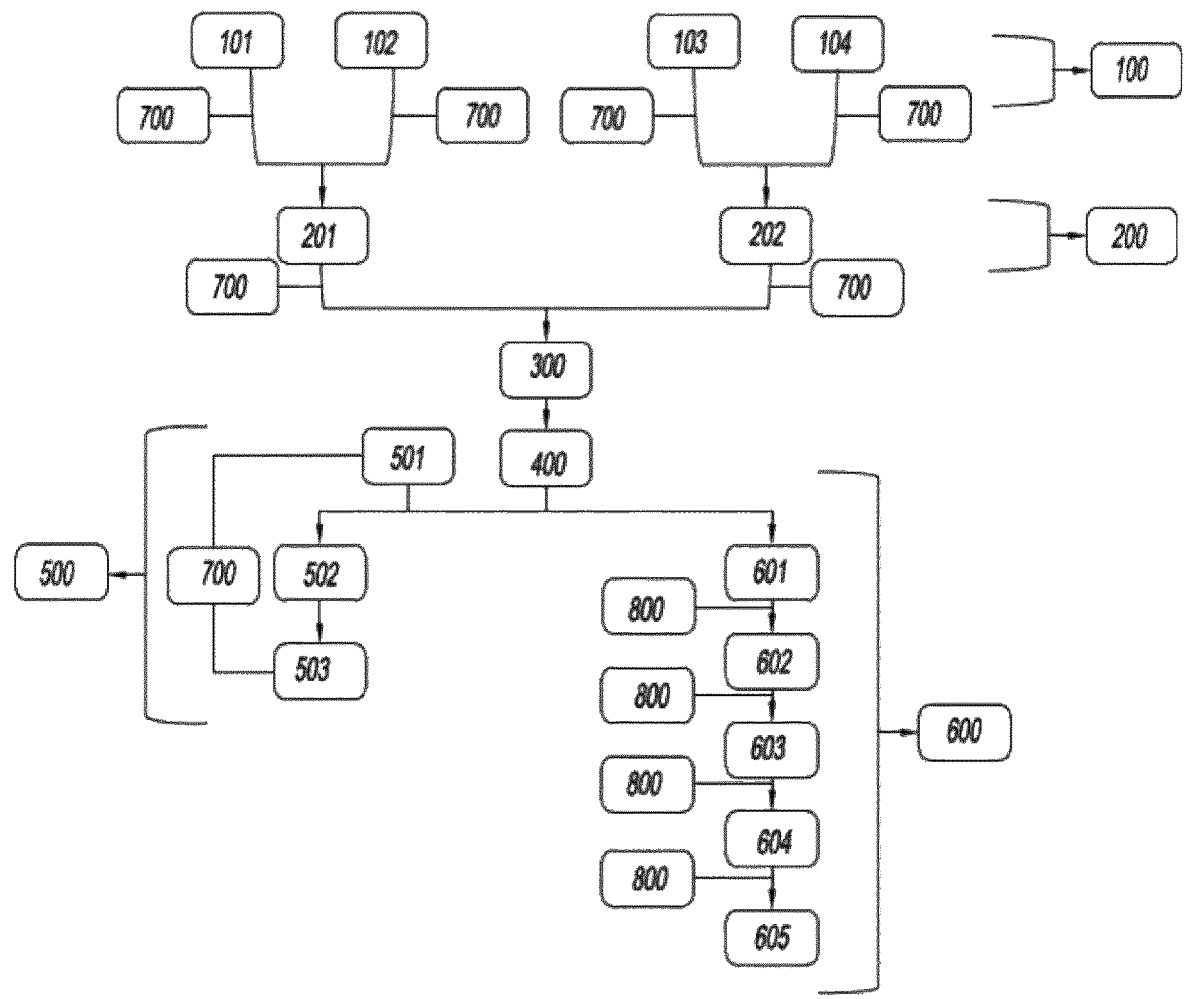
FIG. 1 shows a method for producing fluorapatite crystals as described herein.

The present disclosure provides a method for producing fluorapatite crystals, the method comprising the steps of:
a) providing a first aqueous solution comprising a phosphate source and a fluoride source, said first aqueous solution being supersaturated with respect to the phosphate source and the fluoride source,
b) providing a second aqueous solution comprising a calcium source,
c) mixing the first aqueous solution and the second aqueous solution thereby providing a mixture comprising fluorapatite crystals and a further aqueous solution,
d) optionally stirring the mixture of step c),
e) optionally heating the mixture of step c) and/or step d),
f) separating the fluorapatite crystals from the further aqueous solution,
g) optionally drying the fluorapatite crystals of step f), and
h) optionally milling the fluorapatite crystals obtained in step f) or step g).

The second aqueous solution may be unsaturated with respect to the calcium source. Thus, there is provided a method for producing fluorapatite crystals, the method comprising the steps of:
a) providing a first aqueous solution comprising a phosphate source and a fluoride source, said first aqueous solution being supersaturated with respect to the phosphate source and the fluoride source,
b) providing a second aqueous solution comprising a calcium source, said second aqueous solution being unsaturated with respect to the calcium source,
c) mixing the first aqueous solution and the second aqueous solution thereby providing a mixture comprising fluorapatite crystals and a further aqueous solution,
d) optionally stirring the mixture of step c),
e) optionally heating the mixture of step c) and/or step d),
f) separating the fluorapatite crystals from the further aqueous solution,
g) optionally drying the fluorapatite crystals of step f), and
h) optionally milling the fluorapatite crystals obtained in step f) or step g).

It will be appreciated that step c) of the method described herein may be performed at room temperature, such as from about 20° C. to about 25° C., such as 20° C.±2° C. Further, it will be appreciated that the method described herein may be performed at room temperature and/or may be free from pH adjuster(s). Further, the method may be performed with only little stirring such as stirring for 60 minutes or less, such as 5, 10, 15, 20 25 or 30 minutes. Surprisingly, it has been found that the method allows for fast formation of fluorapatite crystals such as formation of fluorapatite crystals within an hour or less such as about ten minutes, such as about one minute. Moreover, the method allows for producing fluorapatite crystals of various morphologies and/or sizes, such as nanofluorapatite crystals or microfluorapatite crystals. The method also allows for keeping the use of water down. Further, the method allows for keeping the use of energy down since it may be performed at room temperature. As a result, the method is environmentally friendly.

As used herein, the term "supersaturated solution" is understood to mean a solution containing more solute(s) than is predicted by its/their solubility limit, i.e. the limit for how much of the solute(s) that can be dissolved, in a solvent at a specific temperature and/or pressure. For instance, an aqueous solution comprising a phosphate source such as a phosphate source as described herein and/or a fluoride source such a fluoride source as described herein may be supersaturated with respect to the phosphate source and/or the fluoride source. For instance, an aqueous solution such as a first aqueous solution as described herein may be supersaturated with respect to the phosphate source and/or the fluoride source at room temperature and/or atmospheric pressure. In a further example, there is provided a first aqueous solution as described herein which is supersaturated with respect to the phosphate source and the fluoride at room temperature and/or atmospheric pressure.

As used herein, the term "unsaturated solution" is understood to mean that the solute(s) is/are present in solution in a concentration that is lower than its solubility at equilibrium such as equilibrium at room temperature and/or atmospheric pressure. For instance, an aqueous solution comprising a calcium source as described herein, such as a second aqueous solution comprising a calcium source as described herein, may be unsaturated with respect to the calcium source.

The first aqueous solution and the second aqueous solution may be provided in volumes of equal size. Further, the mixing of step c) takes place by adding the first aqueous solution and the second aqueous solution to a container such as simultaneously to a container.

The phosphate source may be selected from the group consisting of monosodium phosphate, disodium phosphate, trisodium phosphate, monosodium diphosphate, disodium diphosphate, trisodium diphosphate, tetrasodium diphosphate, and combination(s) thereof. For instance, the phosphate source may comprise or consist of disodium phosphate such as sodium phosphate dibasic dodecahydrate.

The fluoride source may comprise or consist of sodium fluoride and/or sodium bifluoride.

The calcium source may comprise or consist of calcium chloride, and/or calcium phosphate.

The present disclosure also provides a method as described herein, wherein
step d) is present, and/or
step e) is present or absent.

The molar ratio of the calcium source/the phosphate source/the fluoride source in the method described herein may be about 2-10/3/1 such as about 2.5/3/1 or about 5/3/1.

The fluorapatite crystals produced in accordance with the method described herein may be nanofluorapatite crystals such as nanofluorapatite crystals having a largest dimension, such as a length, within the range of from about 1 nanometer to about 990 nanometers, such as from about 25 nanometers to about 300 nanometers.

The first aqueous solution of the method described herein may further comprise lactic acid. As a result, the fluorapatite crystals formed may be microfluorapatite crystals such as microfluorapatite crystals having a largest dimension, such as a length, within the range of from about 1 micrometer to about 20 micrometers, such as from about 2 micrometers to about 20 micrometers.

The first aqueous solution of the method described herein may be obtained or obtainable by applying heat and/or reduced pressure to an aqueous solution comprising the phosphate source and the fluoride source. In this way, supersaturation is achieved in a convenient manner.

There is also provided a method as described herein wherein step h) is present or absent.

The present disclosure also provides a method for preparing a dental or non-dental composition, said method comprising the steps of:
(i) preparing fluorapatite crystals according to the method for producing fluorapatite crystals described herein, and
(ii) mixing the fluorapatite crystals obtained in step (i) with an additive thereby providing the dental or non-dental composition.

There is also provided a use of fluorapatite crystals produced in accordance with the method for preparing fluorapatite crystals as described herein for making a dental or non-dental composition.

The additive described herein may comprise or consist of one or more of the following: a polymer, an adhesive such as a dental adhesive, a metal oxide such as zinc oxide and/or magnesium oxide.

The dental or non-dental composition described herein may comprise or consist of one or more of the following: a sealer, a ceramic material, a dental restorative product, a filling material such as a dental cement composition; a coating for teeth, an implant, a medical device. For instance, the dental or non-dental composition may comprise or consist of one or more of the following: a liner such as a microliner, a ceramic material.

The method for producing fluorapatite crystals described herein may be performed as shown in FIG. 1.

Further, the method for producing fluorapatite crystals described herein may be described as follows with reference to FIG. 1.

In FIG. 1, the numbers have the following meaning.
100 stands for reactants. For instance, the reactant may be provided as a first or second aqueous solution as described herein.
101 stands for water or an aqueous of lactic acid as described herein
102 stands for a phosphate source and/or a fluoride source as described herein. For instance, the phosphate source and/or fluoride source may be provided as an aqueous solution comprising the phosphate source.
103 stands for water.
104 stands for a calcium source as described herein such as calcium chloride. For instance, the calcium source may be provided as a second aqueous solution as described herein.
200 stands for reacting solution(s) and/or stock solution.
201 stands for a phosphate and fluoride source solution, i.e. a PFS.
202 stands for a calcium source solution, i.e. a CS.
300 stands for container.
400 stands for filtering and/or washing, and/or a filter.
500 stands for separation of by-products from crystals and storage thereof.
501 stands for a pump.
502 stands for water and by-products.
503 stands for storing container of water and/or by-products.
600 stands for drying and/or milling.
601 stands for washing of slurry.
602 stands for drying.
603 stands for drying and collection of powder.
604 stands for fine powder.
605 stands for storage of fine powder.
700 stands for stored reactants and/or container and/or connection.
800 stands for rolling band.

The reactants used in the method described herein, 100, as in previously mentioned methods for producing fluorapatite, are based on the reactants firstly suggested by Montel G. in 1958. The phosphate source, 102, may include monosodium phosphate anhydrous, monosodium phosphate monohydrate, monosodium phosphate dihydrate, disodium phosphate anhydrous, disodium phosphate dihydrate, disodium phosphate heptahydrate, disodium phosphate octahydrate, disodium phosphate dodecahydrate, trisodium phosphate anhydrous (cubic), trisodium phosphate anhydrous (hexagonal), trisodium phosphate hemihydrate, trisodium phosphate hexahydrate, trisodium phosphate octahydrate, trisodium phosphate dodecahydrate, monosodium diphosphate anhydrous, disodium diphosphate anhydrous, disodium diphosphate hexahydrate, trisodium diphosphate anhydrous, trisodium diphosphate monohydrate, trisodium diphosphate nonahydrate, tetrasodium diphosphate anhydrous, tetrasodium diphosphate decahydrate or a combination thereof. The calcium source, 104, may include calcium chloride, calcium chloride dihydrate, calcium chloride hexahydrate, calcium phosphate or a combination thereof. The fluoride source, 102, may include sodium fluoride, sodium bifluoride or a combination thereof.

The reacting solutions may be two and may be similar in volume, 200, and include a phosphate and fluoride source solution (PFS), 201, and a calcium source solution (CS), 202. The aforementioned solutions may be aqueous solutions. The PFS solution is supersaturated and the CS may be unsaturated. A typical PFS solution may be constituted by sodium phosphate dibasic ($Na_2HPO_4$), sodium fluoride (NaF) and an aqueous solution of lactic acid or water, 101. Once the constituents of the PFS are mixed in an independent container connected to the stored reactants, 700, the resultant solution requires a heating period in order to reach supersaturation. The required temperature varies from 35° C. or 55° C., depending on the concentration of lactic acid. A typical CS solution is constituted by calcium chloride 104, $CaCl_2$, and water, 103. The CS solution experiences an exothermic period when the calcium chloride is mixed with water. The temperature that is momentarily achieved varies from the 30° C. to 55° C. depending on the calcium chloride ($CaCl_2$) concentration.

The reacting solutions may be stored as stock solutions, 201 and 202, respectively, for industrially practical reasons. The mixing and stirring of the reacting solutions occurs at room temperature such as from about 20° C. to about 25° C., such as 20° C.±2° C. in a separate container connected (700) to the stored stock solutions, 200. As used herein, room temperature intends a temperature from about 20° C. to about 25° C., such as 20° C.±2° C.

In this container 300 is where the synthesis of the nano- or microcrystals occurs The mixture can be stirred (such as at about 100 rpm) or not, depending on the size and morphology desired. A white precipitate is formed in most of the cases after stirring. Once the mixture has been stirred it may be heated to 70° C. and left at that temperature for about 10 minutes or it can be immediately filtered after stirring, depending on the size and morphology desired. This solution produced in the reaction container is then filtered and washed, 400, the filter can be paper-, polymer- or metal-based. The filtering may use a pump, 501, that is connected, 700, to the storing container of the water and by-products, 503, where the water and byproducts are stored, 502, which is in turn connected, 700, to the filter, 400. By that process the by-products are separated from the crystals and stored, 500. After washing the slurry (601), the drying and milling process is performed, 600. This process, 600, can be performed on a rolling band, 800, to facilitate the automation of the processes. The drying process, 602, can be performed by lowering the pressure in a closed container which contains the slurry, centrifugation, micro-wave radiation or thermal radiation. Subsequently, the dried powder is collected, 603, and may be transported into the milling equipment which may only be required for the nanofluorapatite powders for powder fin, i.e. fine powder, 604. The microfluorapatite powder may not need milling. Milling may be performed in order to break apart agglomerated particles, if present. Further, milling allows for preparing a powder such as a fine powder. Once a fine powder is obtained it can be stored, 605, for further processing.

The disclosure is illustrated by the following non-limitative examples.

EXAMPLES

Abbreviations

SEM stands for Scanning Electron Microscopy.
TEM stands for Transmission Electron Microscope.
EDS stands for Energy Dispersive X-ray spectroscopy
XRD stands for X-ray diffraction or X-ray powder diffractogram
RS stands for Raman spectroscopy
Ca stands for Calcium
P stands for Phosphorous
O stands for Oxygen
Na stands for Sodium
F stands for fluorine
PFS stands for phosphate and fluoride source solution
CS stands for calcium source solution
ISO stands for International organization for Standardization
mm stands for millimeter(s)
nm stands for nanometer(s)
μm stands for micrometer(s)
LED stands for Light-Emitting Diode
MDP stands for Methacryloyloxydecyl dihydrogen phosphate
MPa stands for Mega Pascal
rpm revolutions per minute
w/w weight by weight

Example 1

The reactants used were, calcium chloride ($CaCl_2$, Sigma-Aldrich Lot #BCBS6619V), sodium phosphate dibasic dodecahydrate ($Na_2HPO_4 \cdot 12H_2O$, Sigma Life Science Lot #BCBX3841) and sodium fluoride (NaF, Sigma-Aldrich Lot #SLBK6350V). The calcium, phosphate and fluoride reactants were used in a molar ratio of 2.5/3/1. The process was carried out as described above, with the PFS being supersaturated and the CS unsaturated. Once the PFS and the CS were mixed and stirred for 1 minute at approximately room temperature (20° C.) in the reaction container (300), the mixture was immediately filtered (400), dried and milled (600) without any additional heating.

Figure 3A:
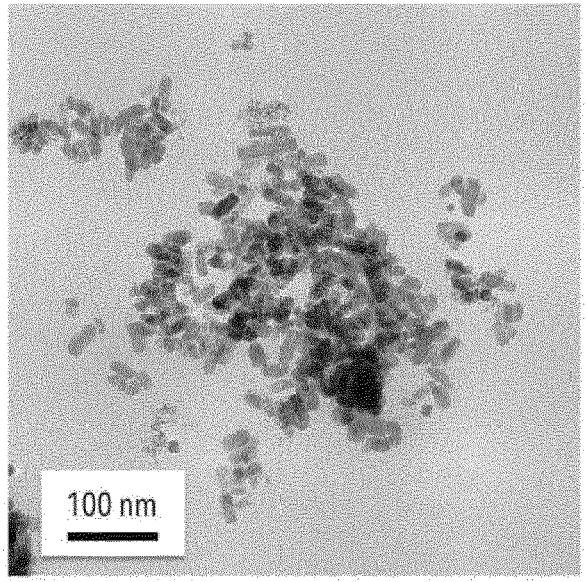
FIG. 3A shows a TEM image of a powder as described in Example 1.
Figure 4:
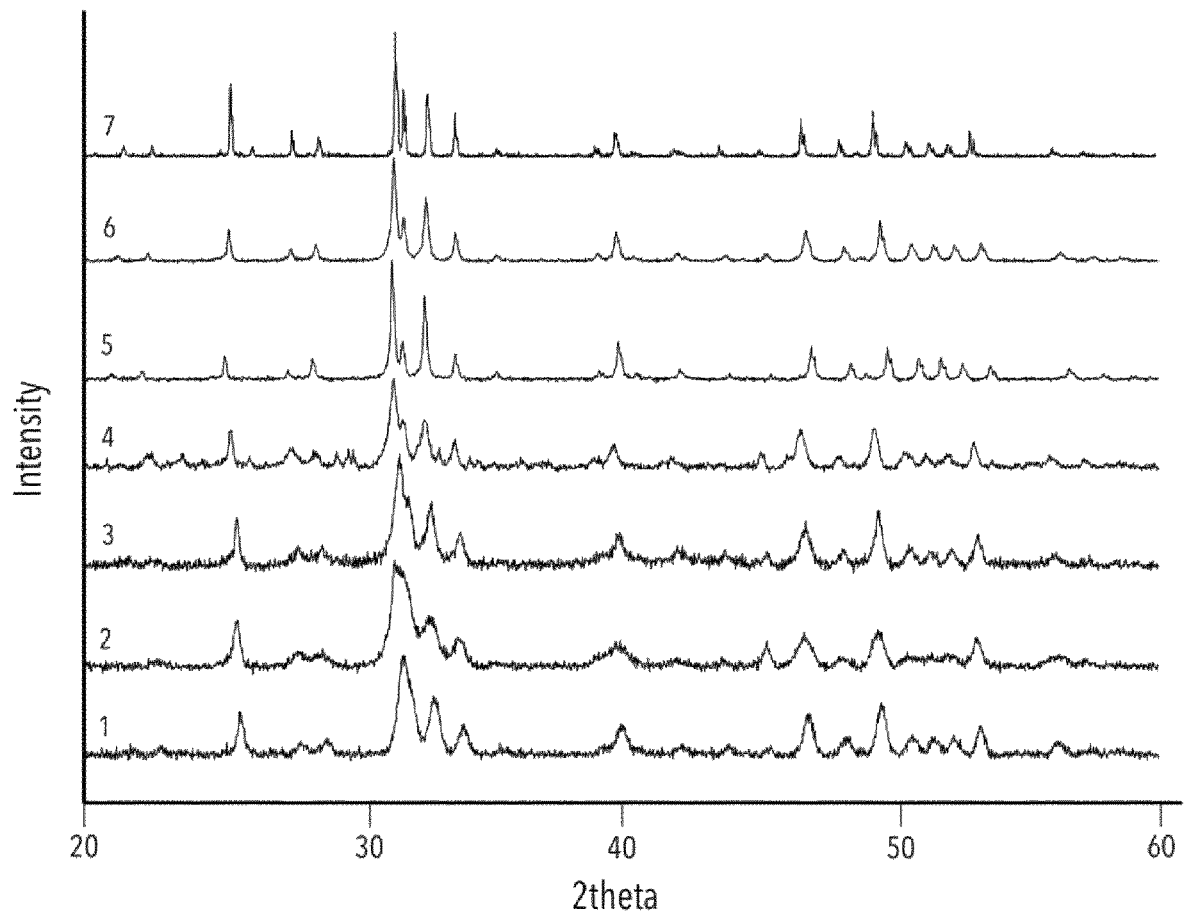
FIG. 4, graph 1, shows an XRD of a powder as described in Example 1.
Figure 5:
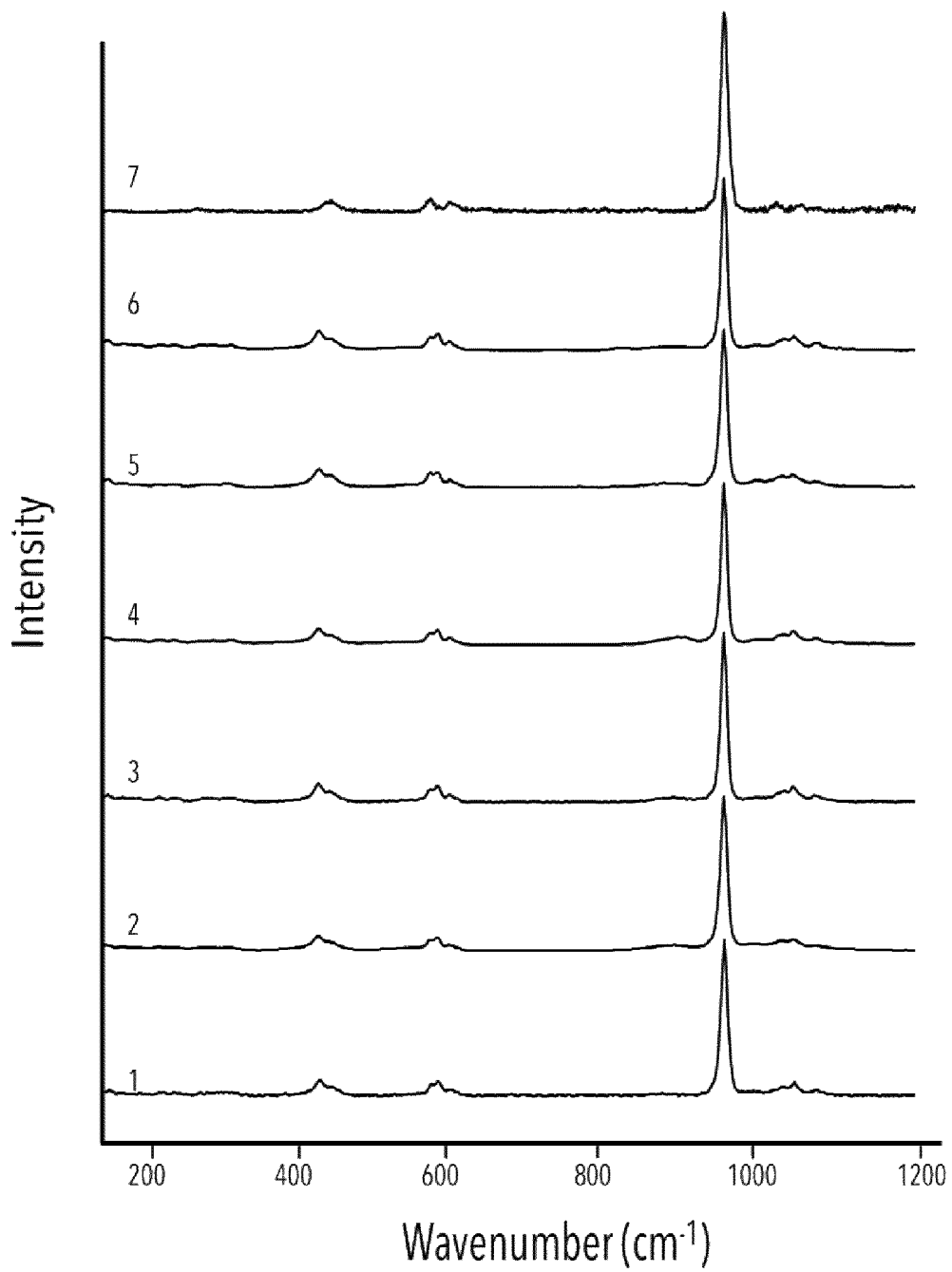
FIG. 5, graph 1, an RS spectrum of a powder as described in Example 1.

The resultant powder was imaged using TEM (FIG. 3A). The powder was also analyzed using XRD (FIG. 4, graph 1) and RS (FIG. 5, graph 1). In FIG. 3A it can be observed crystalline rod-like individual crystals of around 40-60 nm length and 10-15 nm wide. In FIG. 4, graph 1, it can be observed that, the diffractogram corresponds to mineral fluorapatite (brown hexagonal prisms) proceeding from the Levant mine, St. Just, Cornwall, England (FIG. 4, graph 7)

displays the same peaks and diffractogram pattern as FIG. 4, graph 1 (reference 13). The widening of the peaks is a common phenomenon of nanoparticles. The obtained Raman spectra, FIG. 5, graph 1, is also equal to that observed in FIG. 5, graph 7, which corresponds to mineral fluorapatite (pale green hexagonal prisms) proceeding from Fulford, Eagle County, Colorado, USA (Reference 14).

Figure 2A:
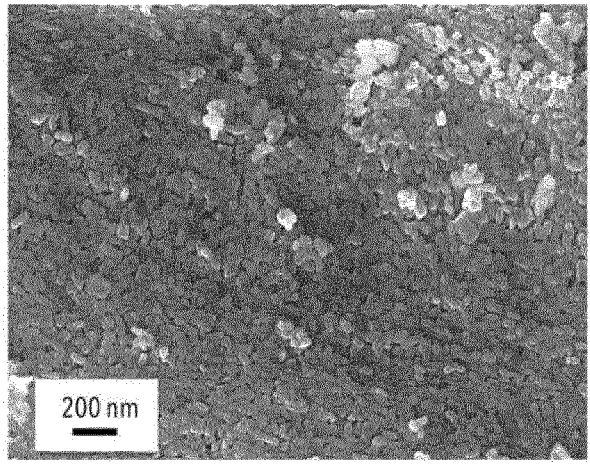
FIG. 2A shows a SEM image of a powder as described in Example 1.
Figure 3B:
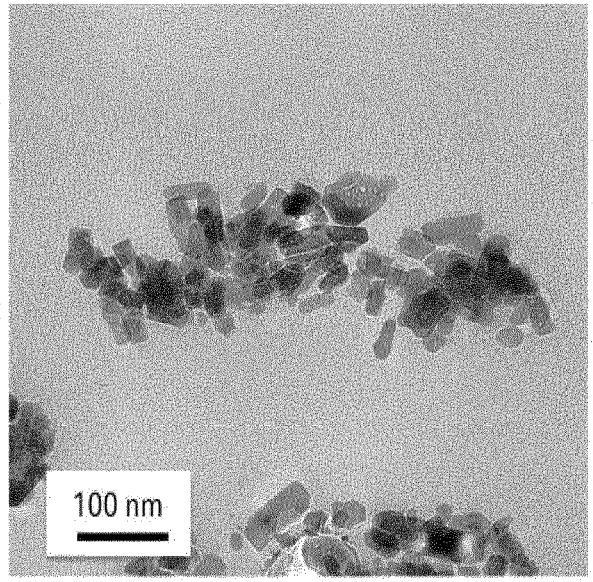
FIG. 3B shows a TEM image of a powder as described in Example 1.
Figure 6:
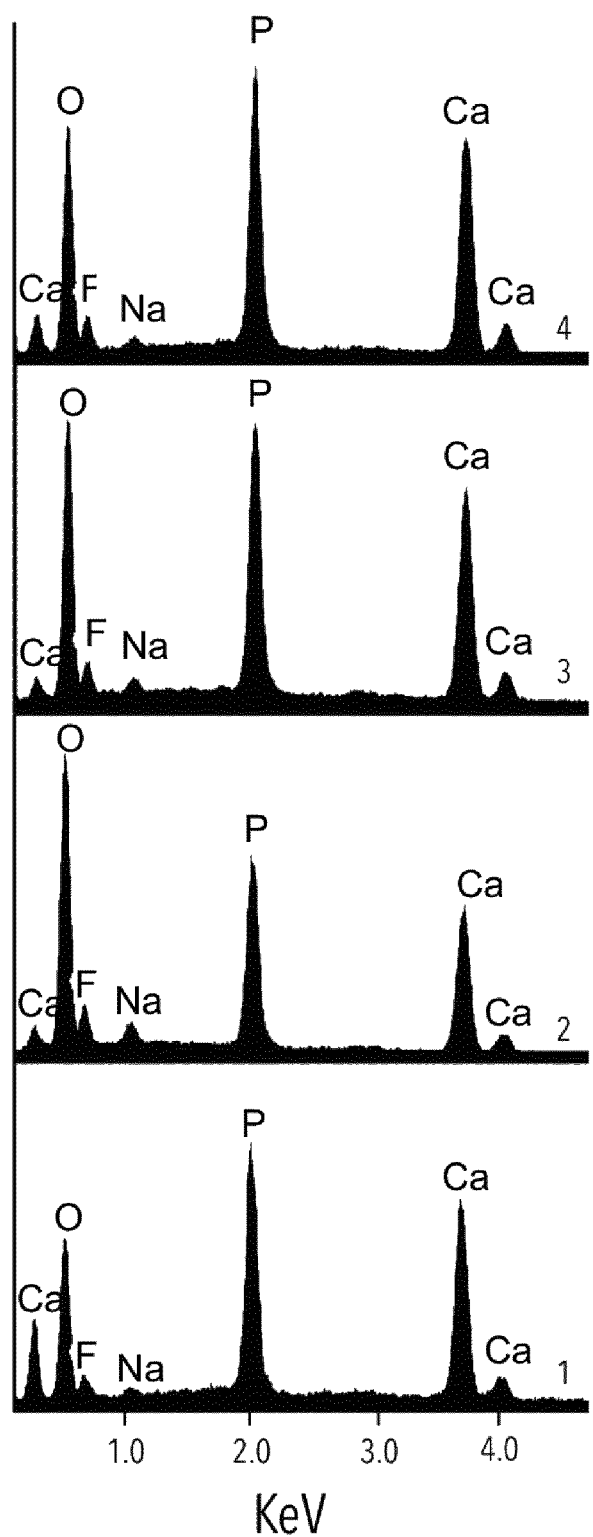
FIG. 6, graph 1, shows an EDS image of a powder as described in Example 1.
Figure 9A:
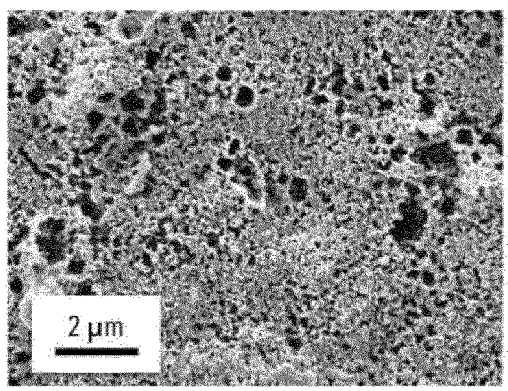
FIG. 9A shows a pellet of a microliner comprising ethanol-based 10-MDP containing adhesive as described in Example 7 after immersion in deionized water.
Figure 9B:
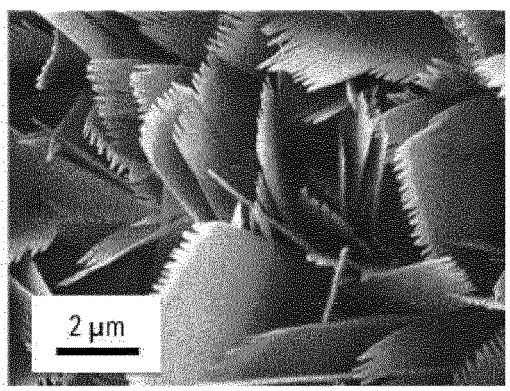
FIG. 9B shows a pellet of a microliner comprising ethanol-based 10-MDP containing adhesive as described in Example 7 after immersion in artificial saliva.
Figure 9C:
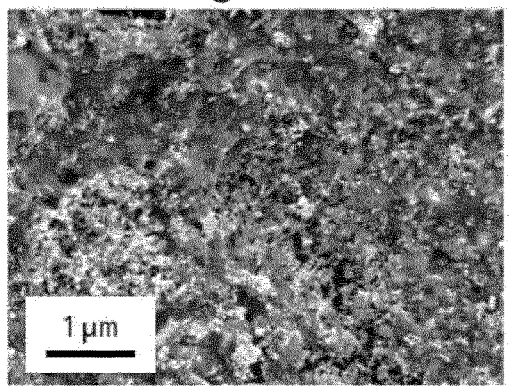
FIG. 9C shows a pellet of a microliner comprising water-based 10-MDP containing primer and an ethanol/water free adhesive as described in Example 7 after immersion in deionized water.
Figure 9D:
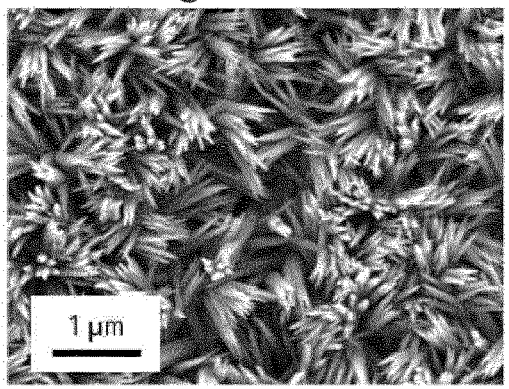
FIG. 9D shows a pellet of a microliner comprising water-based 10-MDP containing primer and an ethanol/water free adhesive as described in Example 7 after immersion in artificial saliva.
Figure 9E:
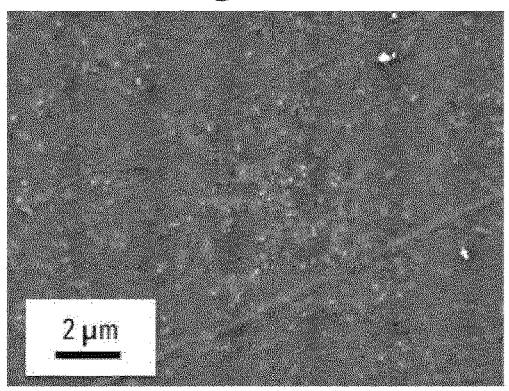
FIG. 9E shows a pellet of a microliner comprising a total etch ethanol-based adhesive as described in Example 7 after immersion in deionized water.
Figure 9F:
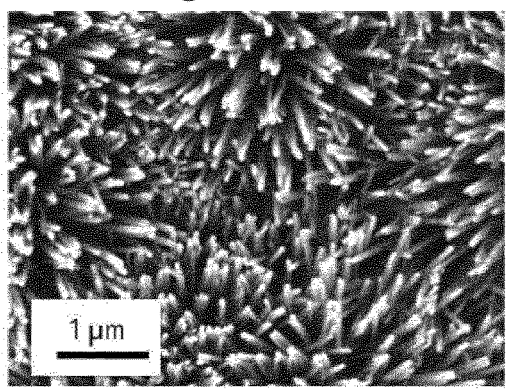
FIG. 9F shows a pellet of a microliner comprising a total etch ethanol-based adhesive as described in Example 7 after immersion in artificial saliva.
Figure 9G:
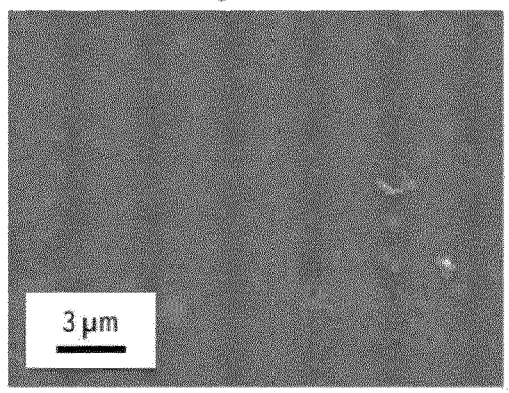
FIG. 9G shows a pellet of a microliner comprising a total etch water-based adhesive adhesive as described in Example 7 after immersion in deionized water.
Figure 9H:
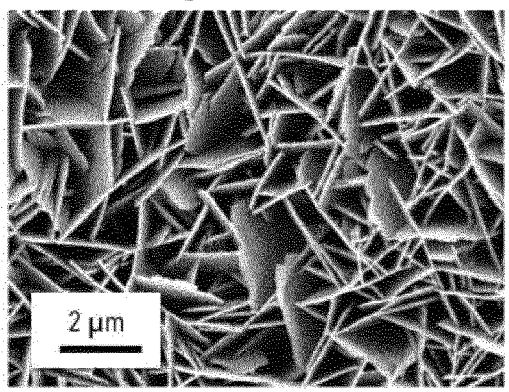
FIG. 9H shows a pellet of a microliner comprising a total etch water-based adhesive adhesive as described in Example 7 after immersion in artificial saliva.

A variation was also performed. The process was carried as initially described, but with 10 minutes of additional heating at 70° C. right after stirring for 1 minute at room temperature (20° C.±2° C.). Resultant powder was imaged using SEM (FIG. 2A), and TEM (FIG. 3B). the powder was also analyzed using XRD (FIG. 4, graph 2), RS (FIG. 5, graph 2) and EDS (FIG. 6, graph 1). In FIG. 2A and in FIG. 3B it can be observed individual rod-like crystals of around 50-100 nm length and 10-50 nm wide. In FIG. 4, graph 2, it can also be seen that its diffractogram is equal to the diffractogram of mineral fluorapatite (FIG. 4, graph 7). Its Raman spectra, FIG. 5, graph 2, is also equal to that observed of mineral fluorapatite (FIG. 5, graph 7). The EDS spectra (FIG. 6, graph 1) showed marked peaks of O, Ca, P, F and Na.

It was concluded that heating, such as heating for 10 minutes at 70° C., slightly increased the size of the crystals.

Example 2

The reactants used were, calcium chloride ($CaCl_2$, Sigma-Aldrich Lot #BCBS6619V), sodium phosphate dibasic dodecahydrate ($Na_2HPO_4 \cdot 12H_2O$, Sigma Life Science Lot #BCBX3841) and sodium fluoride (NaF, Sigma-Aldrich Lot #SLBK6350V). The calcium, phosphate and fluoride reactants were used in a molar ratio of 5/3/1. The process was carried out as previously described, being the PFS supersaturated and the CS unsaturated. Once the PFS and the CS were mixed and stirred for 1 minute at approximately room temperature (20° C.) in the reaction container (denoted 300 in FIG. 1), the mixture was immediately filtered (denoted 400 in FIG. 1), dried and milled (denoted 600 in FIG. 1) without additional heating.

Figure 3C:
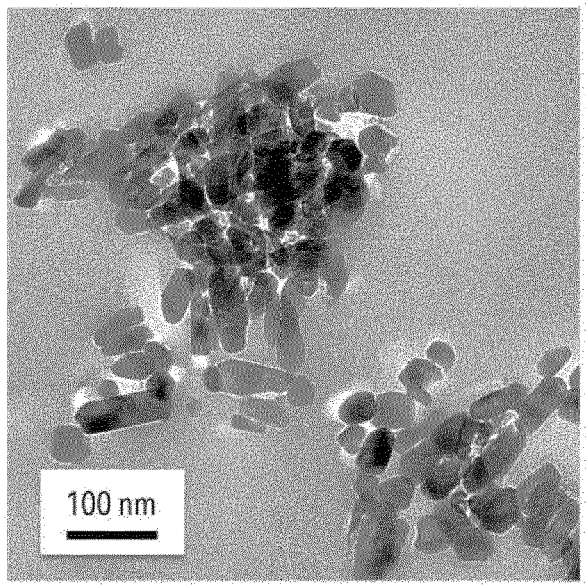
FIG. 3C shows a TEM image of a powder as described in Example 2.

The resultant powder was imaged using TEM (FIG. 3C). The powder was also analyzed using XRD (FIG. 4, graph 3) and RS (FIG. 5, graph 3). In FIG. 3C it can be observed crystalline rod-like individual crystals of around 90-110 nm length and 30-60 nm wide. FIG. 4, graph 3 shows an equal diffractogram as mineral fluorapatite (FIG. 4, graph 7) also displays. It also shows widening of the peaks is a common phenomenon of nanoparticles. The obtained Raman spectra, FIG. 5, graph 3, is also equal to mineral fluorapatite.

A comparison with the powder obtained before heating in Example 1 shows that the resulting crystals in this example were larger than those obtained in Example 1. In the present case, the calcium, phosphate and fluoride reactants were used in a molar ratio of 5/3/1 while in Example 1 the calcium, phosphate and fluoride reactants were used in a molar ratio of 2.5/3/1. Thus, it appears that the size of the obtained crystals can be influenced by the ratio of the calcium source/phosphate source/fluoride source.

Figure 2B:
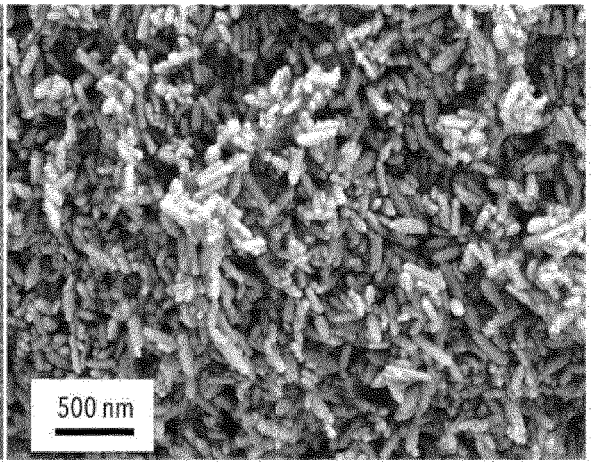
FIG. 2B shows a SEM image of a powder as described in Example 2.
Figure 3D:
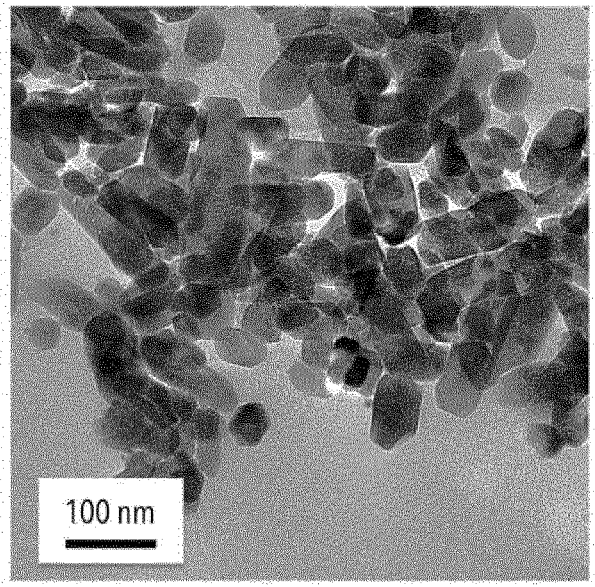
FIG. 3D shows a TEM image of a powder as described in Example 2.

Additionally, the process was carried out as previously described but with 10 minutes of additional heating at 70° C. right after stirring for 1 minute at room temperature (20° C.±2° C.). The resultant powder was imaged using SEM (FIG. 2B) and TEM (FIG. 3D). The powder was also analyzed using XRD (FIG. 4, graph 4), RS (FIG. 5, graph 4) and EDS (FIG. 6, graph 2). In FIG. 2B and in FIG. 3D it can be observed individual rod-like crystals of around 100-150 nm length and 40-90 nm wide. In FIG. 4, graph 4 it can also be seen that its diffractogram is equal to the diffractogram of mineral fluorapatite (FIG. 4, graph 7). Its Raman spectra, FIG. 5, graph 4, is also equal to that observed of mineral fluorapatite (FIG. 5, graph 7). The EDS spectra (FIG. 6, graph 2) showed marked peaks of O, Ca, P, F and Na.

It was concluded that heating, such as heating for 10 minutes at 70° C., increases such as slightly increases the size of the crystals.

Example 3

The reactants used were, calcium chloride ($CaCl_2$, Sigma-Aldrich Lot #BCBS6619V), sodium phosphate dibasic dodecahydrate ($Na_2HPO_4 \cdot 12H_2O$, Sigma Life Science Lot #BCBX3841) and sodium fluoride (NaF, Sigma-Aldrich Lot #SLBK6350V). The calcium, phosphate and fluoride reactants were used in a molar ratio of 5/3/1. The process was carried out as previously described, being the PFS supersaturated and the CS unsaturated. The PFS included an aqueous solution of lactic acid (DL-lactic acid, Sigma Life Science, 85% w/w, Lot #MKBX6004V) at a concentration of 43% weight of the PFS solution. Once the PFS and the CS were mixed and stirred for 1 minute at approximately room temperature (20° C.) in the reaction container (shown as 300 in FIG. 1), the mixture was heated at 70° C. for 10 minutes. Later, the mixture was filtered (shown as 400 in FIG. 1) and dried (shown as 600 in FIG. 1).

Figure 2C:
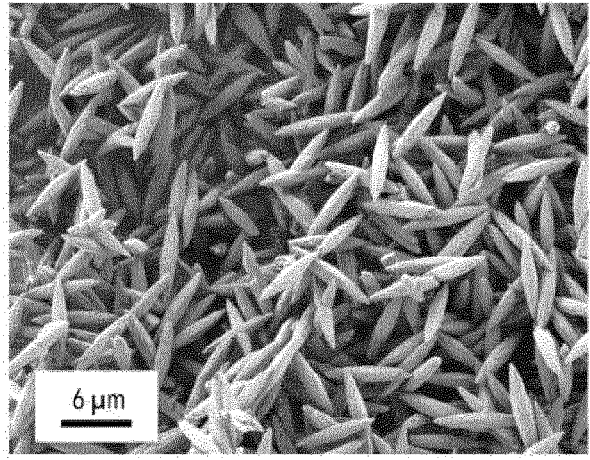
FIG. 2C shows a SEM image of a powder as described in Example 3.

The resultant powder was imaged using a SEM (FIG. 2C). The powder was also analyzed using XRD (FIG. 4, graph 5), RS (FIG. 5, graph 5) and EDS (FIG. 6, graph 3). In FIG. 2C it can be observed individual shuttle-like crystals of around 5.0 µm length and 1.0 µm wide. In FIG. 4, graph 5 it can also be seen that its diffractogram is equal to the diffractogram of mineral fluorapatite (FIG. 4, graph 7). Its Raman spectra, FIG. 5, graph 5, is also equal to that observed of mineral fluorapatite (FIG. 5, graph 7). The EDS spectra (FIG. 6, graph 3) showed marked peaks of O, Ca, P, F and Na.

It was concluded that the presence of lactic acid allowed for formation of crystals having dimensions in the micrometer range.

Example 4

The reactants used were, calcium chloride ($CaCl_2$, Sigma-Aldrich Lot #BCBS6619V), sodium phosphate dibasic dodecahydrate ($Na_2HPO_4 \cdot 12H_2O$, Sigma Life Science Lot #BCBX3841) and sodium fluoride (NaF, Sigma-Aldrich Lot #SLBK6350V). The calcium, phosphate and fluoride reactants were used in a molar ratio of 5/3/1. The process was carried out as previously described, being the PFS supersaturated and the CS unsaturated. The PFS included aqueous solution of lactic acid (DL-lactic acid, Sigma Life Science, 85% w/w, Lot #MKBX6004V) at a concentration of 19% weight of the PFS solution. The PFS and the CS were mixed at approximately room temperature (20° C.) and not stirred in the reaction container (shown as 300 in FIG. 1), the mixture was heated at 70° C. for 10 minutes. Later, the mixture was filtered (shown as 400 in FIG. 1) and dried (shown as 600 in FIG. 1).

Figure 2D:
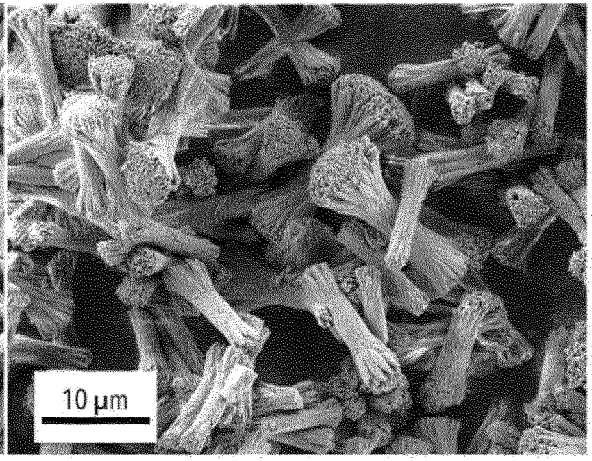
FIG. 2D shows a SEM image of a powder as described in Example 4.

The resultant powder was imaged using SEM (FIG. 2D). The powder was also analyzed using XRD (FIG. 4, graph 6), RS (FIG. 5, graph 6) and EDS (FIG. 6, graph 4). In FIG. 2D it can be observed individual dumbbell crystals of around 10.0 µm length and 4.0 µm wide. In FIG. 4, graph 6 it can also be seen that its diffractogram corresponds to the diffractogram of mineral fluorapatite (FIG. 4, graph 7). Its Raman spectra, FIG. 5, graph 6, is also equivalent to that observed of mineral fluorapatite (FIG. 5, graph 7). The EDS spectra (FIG. 6, graph 4) showed marked peaks of O, Ca, P, F and Na.

It was concluded that the presence of lactic acid allowed for formation of crystals having dimensions in the micrometer range. Further, the amount of lactic acid appears to influence the size of the formed crystals. Further, the lack of stirring appeared to influence the shape of the crystals since in this case the obtained crystals had dumbbell shape whereas the crystals in Example 3 had shuttle-like shape.

Example 5

The powder resultant from Example 2 that underwent additional heating for 10 min was used to produce a polymer-based dental cement. The powder was silanized with 3-methacryloxypropyltrimethosxysilane (Carbosynth, Lot #FM549142001) based on the method reported by Sousa et al 2003 (Reference 15). Later, it was mixed on a pre-heated surface at 60° with Bis-GMA (Carbosynth, Lot #FB1708012001) and TEGDMA (Carbosynth, Lot #FT627491801) in a 70/30 weight ratio. The nanofluorapatite powder corresponded to the 50% of the total weight of the cement. The activator was (+) Camphorquinone (Sigma-Aldrich Lot #31H3611) and the accelerator 2-(Dimethyl-amino)ethyl methacrylate (Tokyo Chemical Industry, Lot #ZKT2I-AT), both used at a 0.1 weight % of the polymer portion of the cement. The cement was then polymerized using a dental curing LED lamp. The resultant polymerized material was white and slightly translucent. A RS spectrum of the polymerized cement is presented in FIG. 7C. To control the bioactivity of the cement, a pellet of 3.0 mm diameter and 1.0 mm thickness was immersed in deionized water and artificial saliva (so-called SAGF medium) at 37° C. for one week. The pellet was dried and then imaged using SEM. It can be observed that in FIG. 7A the nanorods are on the surface but no additional features appear. The pellet that was immersed in artificial saliva was bioactive by showing crystalline structures needle- and blade-like resultant from the interaction of the nanofluorapatite rods with the artificial saliva FIG. 7B.

A biaxial flexural strength test was conducted according to the ISO 4049:2019 (Dentistry—Polymer-based restorative materials). The average biaxial flexural strength was 61.1 (±8.0) MPa, a value that surpasses the required minimum flexural strength for polymer-based dental cements. The hardness of the cement was also measured and compared to the hardness of a flowable composite (Brilliant NanoFlow, Colthene Whaledent, Lot #J68530). The hardness was 39.8 (±4.4) HV1 for the nanofluorapatite polymer-based cement and 40.6 (±2.7) HV1 for the flowable composite. The surface roughness after polishing of the nanofluorapatite polymer-based cement was also measured using interferometry, and also compared to that of the flowable composite. The average surface roughness (Sa) value for the nanofluorapatite polymer-based cement was 0.19 (±0.01) μm and 0.14 (±0.02) μm for the flowable composite.

It was concluded that the crystals produced using the method described herein could be used for manufacturing a dental cement such as a polymer based dental cement.

Example 6

A water-based cement was modified using the powder resultant from Example 2 that underwent additional heating for 10 min. The nanofluorapatite rods accounted for 20% of the weight of the reacting powder. The powder was composed by zinc oxide and magnesium oxide (Harvard cement, Harvard Dental, Lot #91605022) and nanofluorapatite. The liquid by orthophosphoric acid (Harvard cement, Harvard Dental, Lot #1101609). The compressive strength of the cement was measured according to the ISO 9917-1:2007 (Dentistry—Water-based cements—Part 1: Powder/liquid acid-base cements). The average compressive strength was 73.0 (±5.5) MPa. A value that surpasses the required minimum flexural strength for water-based dental cements. An RS spectrum of the modified water-based cement is presented in FIG. 8C. To control the bioactivity of the cement, a pellet of 3.0 mm diameter and 1.0 mm thickness was immersed in deionized water and artificial saliva (SAGF medium) at 37° C. for one week. The pellet was dried and then imaged using SEM. It can be observed that in FIG. 8A the nanorods are on the surface but no additional features appear. The pellet that was immersed in artificial saliva was bioactive by showing crystalline structures blade-like resultant from the interaction of the nanofluorapatite rods with the artificial saliva FIG. 8B.

It was concluded that the crystals produced using the method described herein could be used for manufacturing a dental cement such as a water based dental cement.

Example 7

The powder resultant from Example 2 that underwent additional heating for 10 min was mixed with different dental adhesives to create microliners. A self-etch ethanol-based 10-Methacryloyloxydecyl dihydrogen phosphate (10-MDP)-containing adhesive (Allbond Universal, Bisco, Lot #180006141), a system composed by a water-based 10-MDP containing primer (Clearfil SE bond primer, Kuraray Noritake, Lot #1E0348) and an ethanol/water free adhesive (Clearfil SE bond, Kuraray Noritake, Lot #3F0468), a total etch ethanol-based adhesive (Optibond Solo Plus, Kerr, Lot #7038740) and a total etch water-based adhesive (One Coat, Colthene Whaledent, Lot #189644).

Figure 10:
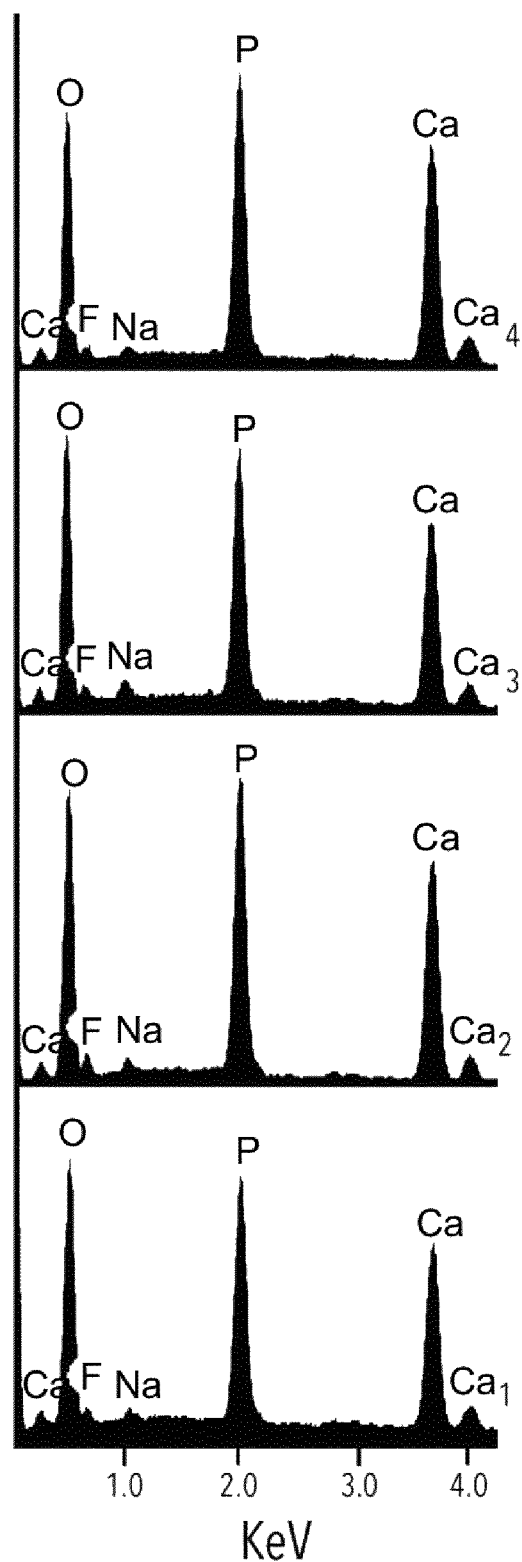
FIG. 10, graph 1, shows an EDS image of a pellet of a microliner comprising ethanol-based 10-MDP containing adhesive as described in Example 7 after immersion in artificial saliva.

To assess the bioactivity of the microliners, a pellet of each mixture 3.0 mm diameter and 1.0 mm thickness was immersed in deionized water and artificial saliva (SAGF medium) at 37° C. for one week. The pellets were dried and then imaged using SEM. It can be observed that all the mixtures that were immersed in deionized water (FIG. 9A, FIG. 9C, FIG. 9E, FIG. 9G) showed no additional surface features compared to the pellets immersed in artificial saliva (FIG. 9B, FIG. 9D, FIG. 9F, FIG. 9H), which in turn, produced crystalline blade- and needle-like structures. The EDS spectra (FIG. 10, graphs 1,2,3,4), of the crystalline structures (FIG. 9B, FIG. 9D, FIG. 9F, FIG. 9H), showed marked peaks of O, Ca, P, F and Na.

Figure 11:
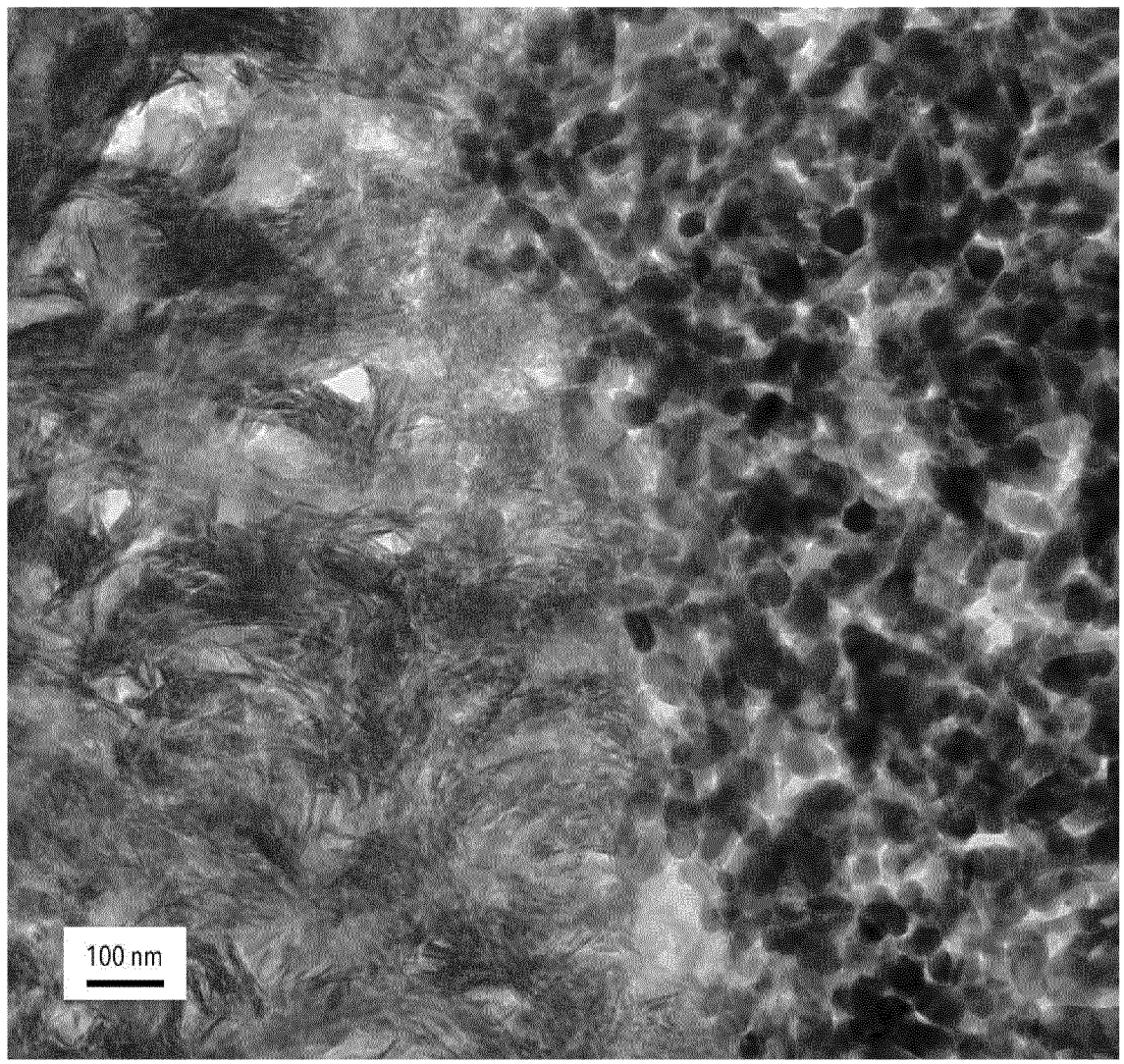
FIG. 11, shows an SEM image of the interface between the microliner comprising ethanol-based 10-MDP containing adhesive and dentin.

A shear-bond strength test was conducted in order to discard any negative effect of the nanofluorapatite crystals on the bond strength of each dental adhesive to human dentin. The test was based on the ISO 29022:2013 (Dentistry—Adhesion—Notched-edge shear bond strength test). The nanofluorapatite powder was mixed at a 1/1 weight proportion with the different adhesives. The total etch water-based adhesive showed an average shear bond value of 17.1 (±4.2) MPa (confidence interval: 14.9-19.5), when mixed with the nanofluorapatite rods the average values was 17.5 (±5.3) MPa (confidence interval: 14.6-20.4). The self-etch ethanol based 10-MDP containing adhesive showed an average shear bond value of 20.1 (±4.6) MPa (confidence interval: 17.6-22.6), when mixed with the nanofluorapatite rods the average values was 21.1 (±5.3) MPa (confidence interval: 18.4-24.3). The total etch ethanol-based adhesive showed an average shear bond value of 24.8 (±6.3) MPa (confidence interval: 21.2-28.2), when mixed with the nanofluorapatite rods the average values was 26.2 (±4.5) MPa (confidence interval: 23.7-28.6). And lastly the system composed by water-based 10-MDP containing primer and an ethanol/water free adhesive showed an average shear bond value of 28.0 (±5.3) MPa (confidence interval: 25.11-30.9), when mixed with the nanofluorapatite rods the average values was 25.0 (±3.6) MPa (confidence interval: 23.05-27.02). No statistically significant differences were found according to a 2-tailed paired t-test, hence, the negative influence on the shear-bond strength by the inclusion of the nanofluorapatite crystals in the adhesives was discarded. A TEM image of the adhesive interface is presented in FIG. 11. The nanofluorapatite rods were mixed with the self-etch ethanol based 10-MDP containing adhesive. A close packaging of the crystals is observed in the adhesive. Also, a close contact with the dentinal tissue results in the formation of a barrier or a microliner.

It was concluded that the crystals produced using the method described herein could be used for manufacturing a dental liner such as a dental microliner.

Example 8

The reactants used were, calcium chloride ($CaCl_2$, Sigma-Aldrich Lot #BCBS6619V), sodium phosphate dibasic dodecahydrate ($Na_2HPO_4 \cdot 12H_2O$, Sigma Life Science Lot #BCBX3841) and sodium fluoride (NaF, Sigma-Aldrich Lot #SLBK6350V). The calcium, phosphate and fluoride reactants were used in a molar ratio of 5/3/1. The process was carried out as previously described, being the PFS supersaturated and the CS was also supersaturated. The PFS and the CS were mixed and stirred at 70 rpm for 1 minute at approximately room temperature (20° C.) in the reaction container (denoted 300 in FIG. 1), the mixture was immediately filtered (denoted 400 in FIG. 1), dried and milled (denoted 600 in FIG. 1) without additional heating. No precipitate was formed immediately after mixing, only after stirring. Analysis using SEM showed formation of a few individual crystals, but on the whole the precipitate was not crystalline. The result of this example was compared with the result obtained in Example 2, and it was concluded that the CS should be unsaturated in order to obtain crystals.

REFERENCES

1. Enax J, Janus A M, Raabe D, Epple M, Fabritius H-O. Ultrastructural organization and micromechanical properties of shark tooth enameloid. Acta Biomaterialia. 2014 September; 10(9):3959-68.
2. Konttinen M-L, HanhijáRjvi H. Fluoride concentrations of the surface enamel of children living in an optimally fluoridated community. European Journal of Oral Sciences. 1986 October; 94(5):427-35.
3. Müller F, Zeitz C, Mantz H, Ehses K-H, Soldera F, Schmauch J, et al. Elemental Depth Profiling of Fluoridated Hydroxyapatite: Saving Your Dentition by the Skin of Your Teeth? Langmuir. 2010 December 21; 26(24): 18750-9.
4. Nedeljkovic I, De Munck J, Vanloy A, Declerck D, Lambrechts P, Peumans M, et al. Secondary caries: prevalence, characteristics, and approach. Clin Oral Investig. 2020 February; 24(2):683-91.
5. Montel G. Contribution à l'étude des mécanismes de synthèse de la fluorapatite. [Paris]; 1958.
6. Farr T D, Tarbutton G, Lewis H T. SYSTEM CaO—P 2 O 5-HF—H2O: EQUILIBRIUM AT 25 AND 50° 1. The Journal of Physical Chemistry. 1962 February; 66(2):318-21.
7. Kniep R, Simon P. Fluorapatite-Gelatine-Nanocomposites: Self-Organized Morphogenesis, Real Structure and Relations to Natural Hard Materials. In: Naka K, editor. Biomineralization I [Internet]. Springer Berlin Heidelberg; 2006 [cited 2016 May 17]. p. 73-125. (Topics in Current Chemistry). Available from: http://link.springer-.com/chapter/10.1007/128_053
8. Chen H, Tang Z, Liu J, Sun K, Chang S-R, Peters M C, et al. Acellular Synthesis of a Human Enamel-like Microstructure. Adv Mater. 2006 Jul. 18; 18(14):1846-51.
9. Chen M, Jiang D, Li D, Zhu J, Li G, Xie J. Controllable synthesis of fluorapatite nanocrystals with various morphologies: Effects of pH value and chelating reagent. Journal of Alloys and Compounds. 2009 Oct. 19; 485(1-2):396-401.
10. Clarkson B H, Chen H. Methods for production and use of synthetic hydroxyapatite and fluorapatite nanorods, and superstructures assembled from the same [Internet]. U.S. Pat. No. 7,879,388 B2, 2011 [cited 2016 Sep. 16]. Available from: http://www.google.se/patents/U.S. Pat. No. 7,879,388
11. Wang H, Sun K, Li A, Wang W, Chui P. Size-controlled synthesis and characterization of fluorapatite nanocrystals in the presence of gelatin. Powder Technology. 2011 May 15; 209(1):9-14.
12. Furukawa A, 古川彰. Method for producing fluorapatite and method for producing fluorapatite particulate [Internet]. JP2014181160A, 2014 [cited 2020 Nov. 27]. Available from: https://patents.google.com/patent/JP2014181160A/en
13. Fluorapatite R060421-RRUFF Database: Raman, X-ray, Infrared, and Chemistry [Internet]. [cited 2021 Jan. 22]. Available from: https://rruff.info/fluorapatite/R060421
14. Apatite R050192-RRUFF Database: Raman, X-ray, Infrared, and Chemistry [Internet]. [cited 2021 Jan. 22]. Available from: https://rruff.info/Apatite/R050192
15. Sousa R A, Reis R L, Cunha A M, Bevis M J. Coupling of HDPE/hydroxyapatite composites by silane-based methodologies. J Mater Sci Mater Med. 2003 June; 14(6): 475-87.

The invention claimed is:
1. A method for producing nanofluorapatite crystals or microfluorapatite crystals, the method comprising the steps of:
   a) providing a first aqueous solution comprising:
      a phosphate source and a fluoride source, and
      optionally lactic acid
      said first aqueous solution being supersaturated with respect to the phosphate source and the fluoride source,
   b) providing a second aqueous solution comprising a calcium source, said second aqueous solution being unsaturated with respect to the calcium source,
   c) mixing the first aqueous solution and the second aqueous solution thereby providing a mixture comprising nanofluorapatite crystals or microfluorapatite crystals and a further aqueous solution,
   d) optionally stirring the mixture of step c),
   e) optionally heating the mixture of step c) and/or step d),
   f) separating the nanofluorapatite crystals or microfluorapatite crystals from the further aqueous solution, g) optionally drying the nanofluorapatite crystals or microfluorapatite crystals of step f), and
h) optionally milling the nanofluorapatite crystals or microfluorapatite crystals obtained in step f) or step g), wherein nanofluorapatite crystals are formed when the first aqueous solution in step a) is free from lactic acid and microfluorapatite crystals are formed when the first aqueous solution in step a) comprises lactic acid.

2. A method for producing nanofluorapatite crystals according to claim 1, the method comprising the steps of:
a) providing a first aqueous solution comprising a phosphate source and a fluoride source, said first aqueous solution being supersaturated with respect to the phosphate source and the fluoride source,
b) providing a second aqueous solution comprising a calcium source, said second aqueous solution being unsaturated with respect to the calcium source,
c) mixing the first aqueous solution and the second aqueous solution thereby providing a mixture comprising nanofluorapatite crystals and a further aqueous solution,
d) optionally stirring the mixture of step c),
e) optionally heating the mixture of step c) and/or step d),
f) separating the nanofluorapatite crystals from the further aqueous solution,
g) optionally drying the nanofluorapatite crystals of step f), and
h) optionally milling the nanofluorapatite crystals obtained in step f) or step g).

3. A method for producing microfluorapatite crystals according to claim 1, the method comprising the steps of:
a) providing a first aqueous solution comprising:
a phosphate source and a fluoride source, and
lactic acid
said first aqueous solution being supersaturated with respect to the phosphate source and the fluoride source,
b) providing a second aqueous solution comprising a calcium source, said second aqueous solution being unsaturated with respect to the calcium source,
c) mixing the first aqueous solution and the second aqueous solution thereby providing a mixture comprising microfluorapatite crystals and a further aqueous solution,
d) optionally stirring the mixture of step c),
e) optionally heating the mixture of step c) and/or step d),
f) separating the microfluorapatite crystals from the further aqueous solution;
g) optionally drying the microfluorapatite crystals of step f), and
h) optionally milling the microapatite crystals obtained in step f) or step g).

4. The method according to claim 1, wherein
the first aqueous solution and the second aqueous solution are provided in volumes of equal size, and/or
the mixing of step c) takes place by adding the first aqueous solution and the second aqueous solution simultaneously to a container.

5. The method according to claim 1, wherein the phosphate source is selected from the group consisting of monosodium phosphate, disodium phosphate, trisodium phosphate, monosodium diphosphate, disodium diphosphate, trisodium diphosphate, tetrasodium diphosphate, and combination(s) thereof.

6. The method according to claim 1, wherein the phosphate source comprises disodium phosphate.

7. The method according to claim 1, wherein the fluoride source is sodium fluoride and/or sodium bifluoride.

8. The method according to claim 1, wherein the calcium source is calcium chloride, and/or calcium phosphate.

9. The method according to claim 1, wherein
step d) is present.

10. The method according to claim 1, wherein the molar ratio of the calcium source/the phosphate source/the fluoride source is 2-10/3/1.

11. The method according to claim 1, wherein
step h) is present.

12. The method according to claim 2, wherein the nanofluorapatite crystals have a largest dimension within the range of from 1 nanometer to 990.

13. The method according to claim 3, wherein the microfluorapatite crystals have a largest dimension within the range of from 1 micrometers to 20 micrometers.

14. The method according to claim 1, wherein the first aqueous solution is obtained by applying heat and/or reduced pressure to an aqueous solution comprising the phosphate source and the fluoride source.

15. The method according to claim 1, wherein the phosphate source comprises phosphate dibasic dodecahydrate.

16. The method according to claim 1, wherein the microfluorapatite crystals have a largest dimension within the range of from 25 nanometers to 300 nanometers.

17. The method according to claim 1, wherein the microfluorapatite crystals have a largest dimension within the range of from 2 micrometers to 20 micrometers.

18. The method according to claim 1, wherein the first aqueous solution comprises from 16% by weight to 36% by weight of lactic acid.

19. The method according to claim 9, wherein step e) is present.

20. The method according to claim 9, wherein step e) is absent.

* * * * *